United States Patent [19]

Nakatani et al.

[11] Patent Number: 5,055,581

[45] Date of Patent: Oct. 8, 1991

[54] BIS(PIPERAZINYLALKYL) ETHER COMPOUND AND METHOD FOR THE PREPARATION THEREOF

[75] Inventors: Keiichi Nakatani; Nobuyasu Nakasugi, both of Kyoto, Japan

[73] Assignee: San-Apro Limited, Kyoto, Japan

[21] Appl. No.: 518,015

[22] Filed: May 2, 1990

[30] Foreign Application Priority Data

May 19, 1989 [JP] Japan .................. 1-127400

[51] Int. Cl.$^5$ .......................... C07D 241/04
[52] U.S. Cl. ................................ 544/235
[58] Field of Search ......................... 544/235

[56] References Cited

U.S. PATENT DOCUMENTS 4,898,876 2/1990 Fujii et al. ................. 544/235

Primary Examiner—Maurice J. Welsh
Assistant Examiner—Rachel Johnson
Attorney, Agent, or Firm—Wyatt, Gerber, Burke & Badie

[57] ABSTRACT

The invention provides a novel compound which is a bis(4-alkyl-substituted piperazinylalkyl) ether such as bis[2-(4-methylpiperazinyl)ethyl] ether and bis[2-(4-ethylpiperazinyl)ethyl] ether. The compound, which can be prepared by the dehydrochlorination reaction between a 1-alkyl-substituted piperazine and a bis(-chloroalkyl) ether, is useful as a catalyst for the urethane-forming reaction between a polyisocyanate compound and a polyol compound to give an advantage that a sufficiently long mixing time is available to ensure full uniformity of the reaction mixture before substantial proceeding of the reaction.

6 Claims, No Drawings

BIS(PIPERAZINYLALKYL) ETHER COMPOUND AND METHOD FOR THE PREPARATION THEREOF

BACKGROUND OF THE INVENTION

The present invention relates to a bis(piperazinylalkyl) ether compound which is a novel compound not known in the prior art nor described in any literature as well as a method for the preparation thereof. The inventive bis(piperazinylalkyl) ether compound has an activity and is useful as a catalyst for the urethane-forming reaction between a polyisocyanate compound and a multifunctional active hydrogen-containing compound, e.g., polyol compound.

Various compounds including amine compounds such as bis(2-dimethylamino ethyl) ether and N,N,N',N',N"-pentamethyl diethylene triamine are known and used as a catalyst for the urethane-forming reaction between a polyisocyanate compound and a multifunctional active hydrogen-containing compound. A problem in these amine compounds as a urethane-forming catalyst is that the activity of these compounds is strong enough even at a relatively low temperature of, e.g., room temperature, at the initial stage of the urethane-foaming reaction or, in other words, the so-called cream time, i.e. the time before the start of the foaming reaction, is extremely short, so that the urethane-forming reaction has pro-ceeded so far already before the reactants, i.e. the polyisocyanate and polyol compounds, can be fully and uniformly blended together to form a uniform reaction mixture even by undertaking a most powerful mixing means.

Accordingly, it is eagerly desired to develop a novel catalytic compound for the urethane-forming reaction which exhibits a relatively low activity when the temperature of the reaction mixture is low at the initial stage of the urethane-forming reaction so that the reactiom proceeds moderately slowly to provide a sufficient time for preparing a uniform mixture of the reactants while exhibiting full activity at an elevated temperature to rapidly complete the reaction.

SUMMARY OF THE INVENTION

The inventors accordingly have conducted extensive investigations to discover a novel catalytic compound to meet the above described requirement and, after synthesizing and testing a large number of amines and related compounds as a catalyst for the urethane-forming reaction, unexpectedly arrived at a discovery that certain bis(piperazinylalkyl) ether compounds are quite satisfactory for the purpose leading to completion of the present invention after conducting detailed studies on the method for the preparation of the compound.

Thus, the invention provides a novel compound which is a bis[2-(4-alkylpiperazinyl)ethyl] ether compound represented by the general formula

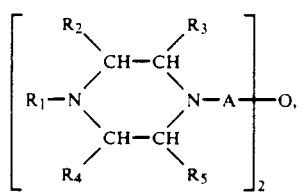 (1)

in which $R_1$ is a methyl group or ethyl group, $R_2$, $R_3$, $R_4$ and $R_5$ are, each independently from the others, a hydrogen atom, methyl group or ethyl group and A is a divalent hydrocarbon group selected from the class consisting of ethylene $-CH_2-CH_2-$, n-propylene $CH_2-CH_2-CH_2-$ and isopropylene $-CH_2-CH(CH_3)-$ groups.

The above defined bis(piperazinylalkyl) ether compound can be synthesized by the dehydrohalogenation reaction between a piperazine compound represented by the general formula

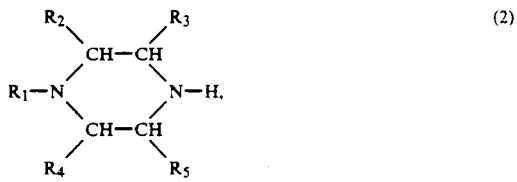 (2)

in which each symbol has the same meaning as defined above, and a bis(haloalkyl) ether compound represented by the general formula

$$X-A-O-A-X, \quad (3)$$

in which A has the same meaning as defined above and X is an atom of halogen such as chlorine, bromine and iodine or, preferably, chlorine, in the presence of a hydrogen halide acceptor.

The above defined bis(piperazinylalkyl) ether compound or a salt thereof is useful as a catalyst for the urethane-forming reaction between a polyisocyanate compound and a multifunctional active hydrogen-containing compound.

DETAILED DESCRIPTION OF THE PREFERRED EMBODIMENTS

As is described above, the bis(piperazinylalkyl) ether compound of the invention is represented by the general formula (1), in which $R_1$ is a methyl group or ethyl group, $R_2$, $R_3$, $R_4$ and $R_5$ are, each independently from the others, a hydrogen atom, methyl group or ethyl group and A is a divalent hydrocarbon group selected from the class consisting of ethylene $-CH_2-CH_2-$, n-propylene $-CH_2-CH_2-CH_2-$ and isopropylene $-CH_2-CH(CH_3)-$ groups. It is preferable that each of $R_2$, $R_3$, $R_4$ and $R_5$ is a hydrogen atom and A is an ethylene group when the compound is to be used as a catalyst for the urethane-forming reaction in respect of the availability of the starting reactants and the adequately high catalytic activity.

Particular examples of the inventive bis(piperazinylalkyl) ether compound include: bis[2-(4-methylpiperazinyl)ethyl] ether; bis[2-(4-ethylpiperazinyl)ethyl] ether; bis[2-(3,4-diethylpiperazinyl)ethyl] ether; bis[2-(2,4-dimethylpiperazinyl)ethyl] ether; bis[2-(3,4-diethylpiperazinyl)ethyl] ether; bis[2-(3,4,5-trimthylpiperazinyl)ethyl] ether; bis[2-(2,4,5-trimethylpiperazinyl)ethyl] ether; bis[2-(4-methylpiperazinyl)propyl] ether; and the like, of which bis[2-(4-methylipiperazinyl)ethyl] ether and bis[2-(4-ethylpiperazinyl)ethyl] ether are preferred as a catalyst for the urethane-forming reaction for the reasons mentioned above.

The bis(piperazinylalkyl) ether compound of the invention forms a salt with various kinds of acids including organic and inorganic acids. Examples of the organic acid include aliphatic carboxylic acids such as monobasic acids, e.g., formic, acetic and octoic acids, and polybasic acids, e.g., succinic and adipic acids, aromatic carboxylic acids such as monobasic acids, e.g., benzoic acid, and polybasic acids, e.g., phthalic and trimellitic acids, phenolic compounds, e.g., phenol and cathechol, and sulfonic acids, e.g., p-toluene sulfonic and methane sulfonic acids. Examples of the inorganic acid include carbonic, hydrochloric, sulfuric, phosphoric and nitric acids.

The bis(piperazinylalkyl) ether compound of the invention can be readily synthesized by the dehydrohalogenation reaction between the piperazine compound represented by the general formula (2) and the bis(haloalkyl) ether compound represented by the general formula (3) in the presence of a hydrogen halide acceptor.

The above mentioned piperazine compound of the general formula (2) is a piperazine compound of which one of the amino groups —NH— is substituted with a methyl or ethyl group. Examples of the piperazine compound include: 1-methyl piperazine; 1-ethyl piperazine; 1,2-dimethyl piperazine; 1,3-dimethyl piperazine; 1,2-diethyl piperazine; 1,3-diethyl piperazine; 1-methyl-2-ethyl piperazine; 1,2,3-trimethyl piperazine; 1,2,6-trimethyl piperazine and the like.

Examples of the bis(haloalkyl) ether compound to be reacted with the above described piperazine compound include: bis(2-chloroethyl) ether; bis(2-bromoethyl) ether; bis(2-iodoethyl) ether; bis(2-chloropropyl) ether; bis(3-chloropropyl) ether; bis(2-bromopropyl) ether and the like.

The dehydrohalogenation reaction between the above described reactants is performed in the presence of a hydrogen halide acceptor. Examples of suitable hydrogen halide acceptor include organic bases such as triethyl amine, pyridine, piperazine compounds and the like and inorganic basic compounds such as alkali metal hydroxides, e.g. sodium and potassium hydroxides, and a salt of such an alkali hydroxide with a weak acid such as carbonic acid, e.g. sodium and potassium carbonates, and the like. It is particularly preferable that the dehydrohalogenation reaction is performed in the presence of the piperazine compound as one of the reactants in an excess amount of, for example, 2 to 4 times of the stoichiometric amount relative to the bis(haloalkyl) ether compound so that the piperazine compound serves both as a reactant and as a hydrogen halide acceptor. The dehydrohalogenation reaction is performed at a temperature in the range from room temperature to 150° C. or, preferably, from 50° to 100° C. The reaction is complete usually within 1 to 15 hours though dependent on the reaction temperature and other conditions. After completion of the reaction, the desired product of the bis(piperazinylalkyl) ether compound is isolated from the reaction mixture by a conventional procedure including distillation under reduced pressure.

As is mentioned before, the inventive bis(piperazinylalkyl) ether compound or a salt thereof can be used as a catalyst for promoting the urethane-forming reaction which is a reaction between a polyisocyanate compound and a multifunctional active hydrogen-containing compound to form a polyurethane resin. If necessary, two kinds or more of the compounds can be used in combination as a catalyst.

Any known polyisocyanate compound conventionally used as a starting material of a polyurethane can be used without particular limitations in the reaction using the inventive bis(piperazinylalkyl) ether compound as a catalyst. Examples of suitable polyisocyanate compound include: aromatic polyisocyanates, e.g., tolylene diisocyanates and diphenyl methane diisocyanate and aliphatic polyisocyanates, e.g., hexamethylene diisocyanate, and isophorone diisocyanate, as well as derivatives thereof, for example, partially modified with a carbodimide, isocyanurate and the like. Also usable are prepolymers containing free isocyanate groups obtained by the partial reaction of the above named polyisocyanate compound and a multifunctional active hydrogen-containing compound. These polyisocyanate compounds can be used either singly or as a mixture of two kinds or more according to need.

The multifunctional active hydrogen-containing compound as a counterpart of the polyisocyanate compound in the urethane-forming reaction includes water, low-molecular polyols, high-molecular polyols and polyamines and they can be used either singly or as a combination of two kinds or more according to need.

Any known low-molecular polyol compounds can be used without particular limitations. Examples of the low-molecular polyol compound include amine-type low-molecular polyols such as triethanol amine and diethanol amine and low-molecular polyols containing no nitrogen atoms such as ethylene glycol, diethylene glycol, butane diol, trimethylol propane, glycerin and 1,4-bis(2-hydroxyethyl) phenylene ether and they can be used either singly or as a combination of two kinds or more according to need.

Any of high-molecular polyols also can be used as a starting material in the urethane-forming reaction without particular limitations. Examples of the high-molecular polyol compound include: polyether polyols as an adduct of an alkylene oxide, e.g., ethylene oxide and propylene oxide, to water, a low-molecular polyol, e.g., ethylene glycol, propylene glycol, glycerin, trimethylol propane, triethanol amine, pentaerithritol, sorbitol and sucrose, or a polyamine, e.g., ethylene diamine, diethylene triamine, tolylene diamine, xylylene diamine, piperazine, N-aminoalkyl piperazine, N,N-dimethylaminoalkyl amines and cyclohexylene diamine; polymeric polyols obtained by the reaction of a polyether polyol and an ethylenically unsaturated monomer, e.g., acrylonitrile, styrene, methyl methacrylate and butadiene (see, for example, U.S. Pat. No. 3,383,351); and polyester polyols obtained by the esterification reaction of a polybasic carboxylic acid, e.g., succinic acid, maleic acid, sebacic acid, adipic acid, fumaric acid, phthalic acid and dimer acid, and a low-molecular polyol compound mentioned above. These high-molecular polyol compounds can also be used either singly or as a combination of two kinds or more according to need.

Any known polyamine compounds can be used as a class of the multifunctional active hydrogen-containing compound. Examples of the polyamine compound include tolylene diamine, xylylene diamine, diamino diphenyl methane and methylene bis-2-chloroaniline and they can be used either singly or as a combination of two kinds or more according to need.

Although the bis(piperazinylalkyl) ether compound or a salt thereof according to the invention alone is fully effective as a catalyst for the urethane-forming reaction, it is optional that the catalyst is a combination of the inventive compound with one or more of conventional catalytic compounds for the urethane-forming reaction. Known catalytic compounds include, for example, 1,4-diazabicyclo(2,2,2)octane, 1,3,5-tris(3-dimethylaminopropyl) hexahydro-s-triazine, N,N,N',N'-tetramethyl hexamethylene diamine, N,N,N-tris(dimethylaminopropyl) amine, N-methyl-N,N-bis(dimethylaminopropyl) amine, N-methyl dicyclohexyl amine, 1,2-dimethylimidazole, 1,8-diazabicyclo(5,4,0) undecene-7 and other amine compounds. When these known amine compounds are used in combination with the inventive bis(piperazinylalkyl) ether compound, the weight proportion of the inventive compound to the known amine compound should not be smaller than 1:10 or, preferably, should not be smaller than 1:4.

It is further optional that the inventive bis(piperazinylalkyl) ether compound is used as a catalyst for the urethane-forming reaction in combination with a metallic compound such as stannous octoate, dibutyl tin dilaurate and tin mercaptide having catalytic activity. When these known metallic compounds are used in combination with the inventive compound, the weight proportion of the inventive compound to the known metallic compound should not be smaller than 1:10 or, preferably, should not be smaller than 1:5.

It is of course optional that the reaction mixture for the preparation of a polyurethane foam or resin by using the inventive compound as a catalyst is admixed with various kinds of known additives such as surface active agents, blowing agents, fillers, coloring agents, antioxidants and the like to serve as a crosslinking agent, emulsifier, stabilizer or foam-conditioning agent.

The catalyst in the urethane-forming reaction, which can be performed according to a known procedure, is used in an amount in the range from 0.01 to 10 parts by weight per 100 parts by weight of the polyol compound in the preparation of a polyurethane foam and in the range from 0.01 to 5 parts by weight per 100 parts by weight of the urethane prepolymer in the preparation of a polyurethane resin.

When the bis(piperazinylalkyl) ether compound of the invention is used as a catalyst for the urethane-forming reaction in the preparation of polyurethane foams, a great advantage is obtained that a much longer cream time is available than in the use of conventional amine-based catalysts still with a gelation time of about the same length to ensure a sufficiently long mixing time of the reactants before the urethane-forming reaction is substantially started contributing to the improvements in the workability and in the product quality. Moreover, the inventive bis(piperazinylalkyl) ether compound has a larger molecular weight and higher boiling point as well as less volatilizability with almost no offensive odor than conventional amine-based catalytic compounds so that the working environments for the manufacture of polyurethane foams can be greatly improved.

In the following, examples are given to illustrate in more detail the inventive bis(piperazinylalkyl) ether compound and the method for the preparation thereof as well as the application of the compound as a catalyst for the preparation of a urethane polymer although the scope of the invention is never limited thereto. The NMR spectral data given in the following examples were obtained by the measurement using deuterated dimethyl sulfoxide, referred to as DMSO-$d_6$, as the medium. The total amine values were determined by the electrometric titration using hydrochloric acid as a titrant. In the following, the term of "parts" always refers to "parts by weight".

EXAMPLE 1

Bis[2-(4-methylpiperazinyl)ethyl] ether was synthesized in the following manner. Thus, 600 g (6.0 moles) of 1-methyl piperazine were taken in a flask equipped with a stirrer, thermometer and reflux condenser and 143 g (1.0 mole) of bis(2-chloroethyl) ether were added dropwise into the flask taking 30 minutes while the reaction mixture was kept at a temperature of 70° to 80° C. under agitation. After completion of the dropwise addition of the reactant, the reaction mixture was further agitated for 3 hours at the same temperature to complete the reaction. Thereafter, 320 g of a 30% by weight aqueous solution of sodium hydroxide were added under agitation to the reaction mixture which was subjected to phase separation into the aqueous lower layer and organic upper layer. The organic phase of the upper layer was taken and distilled under reduced pressure to give 92.9 g of a fraction boiling at 135° to 145° C. under a pressure of 1 mmHg. The data of the $^1$H-NMR spectroscopy and total amine value shown below supported that this fraction was the desired bis[2-(4-methylpiperazinyl)ethyl] ether. The above mentioned yield of the product was 34% of the theoretical value based on the bis(2-chloroethyl) ether.

$^1$H-NMR (DMSO-$d_6$, δ, ppm)

$$\left[ H_3C\underset{1}{-}N \underset{\diagdown}{\overset{\diagup}{\phantom{X}}} \underset{CH_2-CH_2}{\overset{CH_2-CH_2}{\phantom{X}}} \underset{\diagup}{\overset{\diagdown}{\phantom{X}}} N\underset{4}{-}CH_2\underset{5}{-}CH_2- \right]_2 O$$

| | | | | |
|---|---|---|---|---|
| 1 | H$_3$C | 6H | s | 2.12 |
| 2 & 3 | CH$_2$ | 16H | m | 2.14 to 2.49 |
| 4 | CH$_2$ | 4H | t | 2.42 |
| 5 | CH$_2$ | 4H | t | 3.45 |

Total amine value: Determined: 408 mg KOH/g. Calculated: 415 mg KOH/g.

EXAMPLE 2

Bis[2-(4-ethylpiperazinyl)ethyl] ether was synthesized in substantially the same manner as in Example 1 excepting replacement of the 1-methyl piperazine with the same molar amount of 1-ethyl piperazine. The product obtained could be identified to be the desired compound from the data of the $^1$H-NMR spectroscopy and overall amine value shown below.

$^1$H-NMR (DMSO-$d_6$, δ, ppm)

$$\left[ H_3C\underset{1}{-}CH_2\underset{2}{-}N \underset{\diagdown}{\overset{\diagup}{\phantom{X}}} \underset{CH_2-CH_2}{\overset{CH_2-CH_2}{\phantom{X}}} \underset{\diagup}{\overset{\diagdown}{\phantom{X}}} N\underset{5}{-}CH_2\underset{6}{-}CH_2- \right]_2 O$$

| | | | | |
|---|---|---|---|---|
| 1 | H$_3$C | 6H | t | 0.95 |
| 2 | CH$_2$ | 4H | q | 2.22 to 2.30 |
| 3 & 4 | CH$_2$ | 16H | m | 2.14 to 2.49 |
| 5 | CH$_2$ | 4H | t | 2.41 |
| 6 | CH$_2$ | 4H | t | 3.46 |

Total amine value: Determined: 369 mg KOH/g. Calculated: 377 mg KOH/g.

EXAMPLE 3

(Experiments No. 1 to No. 4)

The bis(piperazinylalkyl) ether compound prepared in the above described Example 1 was subjected in Experiment No. 1 to the test for the activity as a catalyst in the urethane-forming reaction to give a rigid polyurethane foam according to the formulation given below:

- 80 parts of a sugar-based polyol having a hydroxyl value of about 440 (SU 464, a product by Mitsui Toatsu Chemicals, Inc.);
- 20 parts of an amine-based polyol having a hydroxyl value of about 450 (ED-450, a product by Mitsui Toatsu Chemicals, Inc.);
- 0.5 part of water;
- 1.5 parts of a silicone-based foam-conditioning agent (SH-193, a product by Toray Silicone Co.);
- 37 parts of Freon-11;
- crude MDI (MDI-CR 200, a product by Mitsui Toatsu Chemicals, Inc.) in an amount corresponding to 110 NCO index; and
- 4 parts of the bis(piperazinylalkyl) ether as a catalyst.

Taking 50 g of the two polyols as a total together with corresponding amounts of the other materials each kept at a temperature of 20° C., the urethane mixture was subjected to foaming according to a conventional procedure in a foaming box having dimensions of 15 cm by 12 cm width and 20 cm depth and the times in seconds taken for processing were recorded including the cream time, referred to as "ct", gelation time, referred to as "gt", and tack-free time, referred to as "tft", to give the results shown in Table 1 below, which also gives the ratio of ct:gt.

The experimental procedure in Experiments No. 2, No. 3 and No. 4, the latter two experiments being undertaken for comparative purpose, was substantially the same as in Experiment No. 1 described above excepting replacement of 4 parts of the bis(piperazinylalkyl) ether compound prepared in Example 1 with 6 parts of the bis(piperazinylalkyl) ether compound prepared in Example 2, with 4 parts of bis(2-dimethylamino ethyl) ether and with 2 parts of N,N,N',N',N''-pentamethyl diethylene triamine, respectively. The processing times in these experiments are also shown in Table 1 below.

TABLE 1

| Experi- | Processing time, seconds | | | Ratio of |
|---------|----|----|-----|----------|
| ment No. | ct | gt | tft | ct:gt, % |
| 1 | 16 | 85 | 140 | 19 |
| 2 | 15 | 88 | 105 | 17 |
| 3 | 7 | 82 | 105 | 8.5 |
| 4 | 4 | 88 | 95 | 4.5 |

As is understood from the results shown in Table 1, each of the bis(piperazinylalkyl) ether compounds of the invention gives about the same gelation time of 85 seconds as in the use of the comparative catalysts while the cream time obtained therewith is 2 to 4 times longer than the cream time obtained with the comparative catalysts. This means that a sufficiently long time is available to complete uniform mixing of the starting materials before a substantial urethane-forming reaction is started in the mixture.

EXAMPLE 4

A foaming test for the preparation of a flexible polyurethane foam was undertaken by using the bis(piperazinylalkyl) ether compound prepared in Example 1 as the catalyst. Thus, 100 parts of a polyol having an average molecular weight of about 3000 and a hydroxyl value of 56 mg KOH/g, which was an addition product of propylene oxide to glycerin (Sannix GP-3000, a product by Sanyo Chemical Industries, Ltd.), 4.5 parts of water, 2 parts of a silicone-based foam-conditioning agent (L-520, a product by Nippon Unicar Co.), 0.2 part of the catalyst and 0.34 part of stannous octoate were mixed together and the mixture was then admixed with 54.8 parts of tolylene diisocyanate (TDI-80, a product by Mitsui Toatsu Chemicals, Inc.) and vigorously agitated for 7 seconds using a high-speed stirrer followed by immediate transfer of the mixture into a carton box so that a flexible polyurethane foam having excellent properties could be obtained with a rise time of 88 seconds.

What is claimed is:

1. A bis[(4-alkylpiperazinyl)alkyl] ether compound represented by the general formula

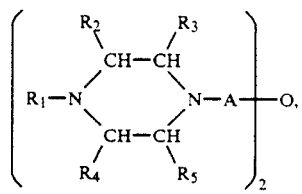

in which $R_1$ is a methyl group or ethyl group, $R_2$, $R_3$, $R_4$ and $R_5$ are, each independently from the others, a hydrogen atom, methyl group or ethyl group and A is a divalent hydrocarbon group selected from the class consisting of ethylene —$CH_2$—$CH_2$—, n-propylene —$CH_2$—$CH_2$—$CH_2$— and isopropylene —$CH_2$—$CH(CH_3)$— groups.

2. The bis[(4-alkylpiperazinyl)alkyl] ether compound as claimed in claim 1 wherein each of $R_2$, $R_3$, $R_4$ and $R_5$ is a hydrogen atom.

3. The bis[(4-alkylpiperazinyl)alkyl] ether compound as claimed in claim 1 wherein the group denoted by A is an ethylene group.

4. A method for the preparation of a bis[(4-alkylpiperazinyl)alkyl] ether compound represented by the general formula

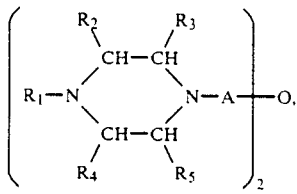

in which $R_1$ is a methyl group or ethyl group, $R_2$, $R_3$, $R_4$ and $R_5$ are, each independently from the others, a hydrogen atom, methyl group or ethyl group and A is a divalent hydrocarbon group selected from the class consisting of ethylene —$CH_2$—$CH_2$—, n-propylene —$CH_2$—$CH_2$—$CH_2$— and isopropylene —$CH_2$—$CH(CH_3)$— groups, which comprises subjecting a piperazine compound represented by the general formula

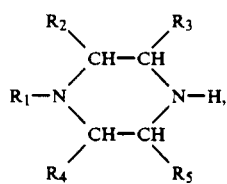

in which each symbol has the same meaning as defined above, and a bis(haloalkyl) ether compound represented by the general formula $$X-A-O-A-X,$$

in which A has the same meaning as defined above and X is an atom of halogen, to a dehydrohalogenation reaction in the presence of a hydrogen halide acceptor.

5. The method for the preparation of a bis[(4-alkyl-piperazinyl)alkyl] ether compound as claimed in claim 4 wherein the halogen atom denoted by X is a chlorine atom.

6. The method for the preparation of a bis[(4-alkyl-piperazinyl)alkyl] ether compound as claimed in claim 4 wherein the piperazine compound serves also as the hydrogen halide acceptor.

* * * * *